United States Patent
Hommeltoft

(10) Patent No.: US 11,555,153 B1
(45) Date of Patent: Jan. 17, 2023

(54) CONVERSION OF GLYCEROL TO FUEL-RANGE ORGANIC COMPOUNDS

(71) Applicant: CHEVRON U.S.A. INC., San Ramon, CA (US)

(72) Inventor: Sven Ivar Hommeltoft, Pleasant Hill, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/723,578

(22) Filed: Apr. 19, 2022

(51) Int. Cl.
*C10G 3/00* (2006.01)
*C10G 65/12* (2006.01)

(52) U.S. Cl.
CPC ............... *C10G 3/49* (2013.01); *C10G 65/12* (2013.01); *C10G 2400/02* (2013.01); *C10G 2400/08* (2013.01)

(58) Field of Classification Search
CPC ...... C10G 3/49; C10G 65/12; C10G 2400/02; C10G 2400/08
See application file for complete search history.

(56) References Cited

U.S. PATENT DOCUMENTS

| 10,781,376 B2 | 9/2020 | Varma et al. | |
| 2014/0051872 A1* | 2/2014 | Blank | B01J 21/066 568/903 |
| 2014/0335586 A1* | 11/2014 | Zhang | C10G 35/04 435/167 |

* cited by examiner

*Primary Examiner* — Thuan D Dang

(57) ABSTRACT

A process for producing fuel-range organic oxygen-containing compounds is provided. The process includes converting glycerol in the presence of a metal oxide catalyst. The fuel-range organic oxygen-containing compounds can be deoxygenated to produce gasoline and jet fuels or fuel blending components.

11 Claims, 1 Drawing Sheet

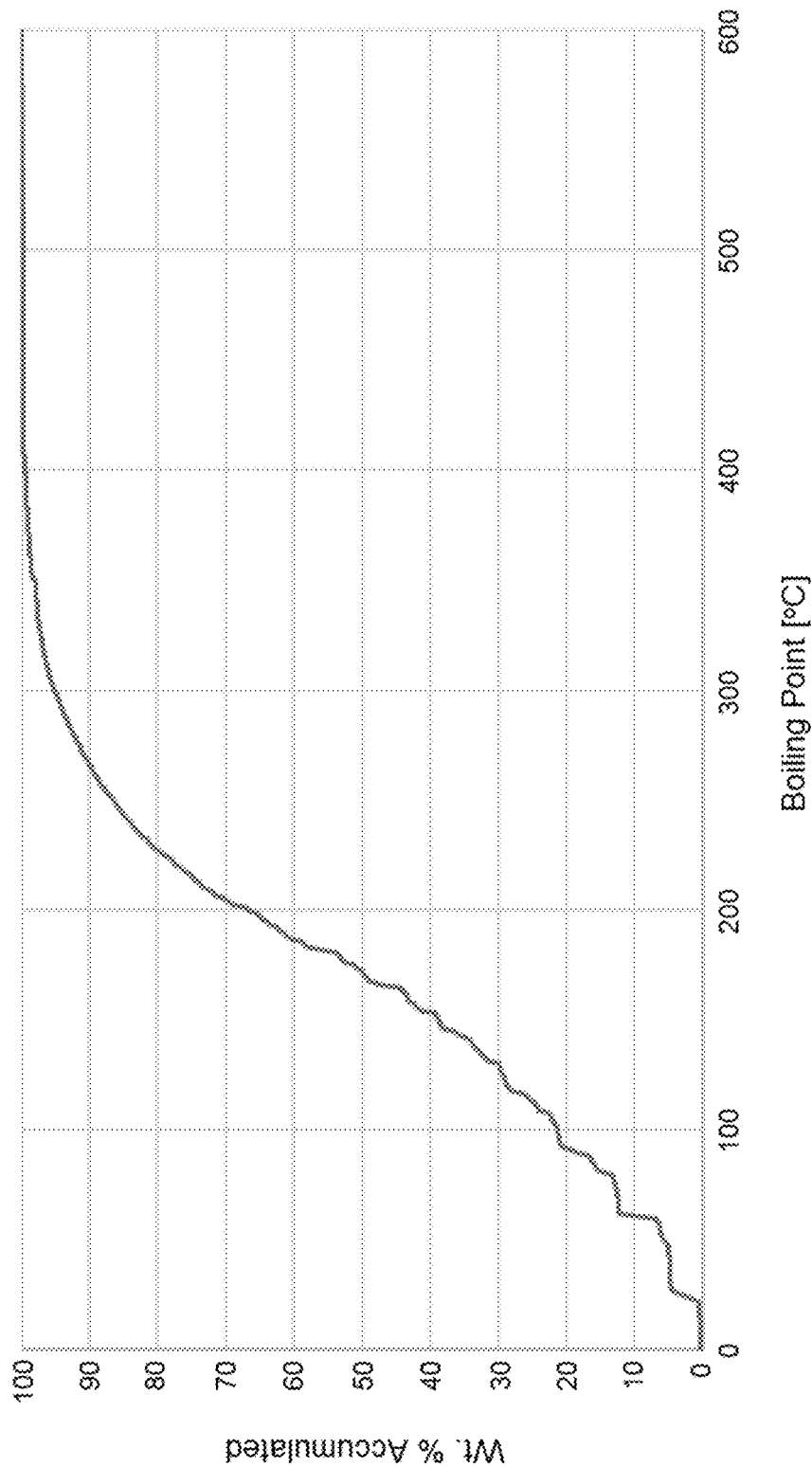

CONVERSION OF GLYCEROL TO FUEL-RANGE ORGANIC COMPOUNDS

FIELD

The present disclosure relates to methods for converting glycerol to organic oxygen-containing compounds boiling in the gasoline and jet range.

BACKGROUND

As the demand for gasoline and jet fuel increases worldwide, there is increasing interest in feedstock sources other than petroleum crude oil.

Glycerol (1,2,3-propanetriol) is produced in large quantities as a by-product in the production of biodiesels. With an increasing focus on the use of biofuels to at least partly replace petroleum fuels, the production of glycerol has increased to levels far higher than current demand. As a result, crude glycerol is a cheap and readily available material, particularly in countries where production of biofuels is prevalent, and there has been an increased focus on the development of suitable applications of glycerol.

Increased production of biodiesel made by transesterification of lipids with light alcohols such as methanol has resulted in production of large volumes of glycerol in a somewhat dilute form and containing varying amounts of dissolved non-volatile salts and other impurities. In this form, glycerol is not suitable in renewable fuels and because of its high content of water and impurities the technical quality formed in biodiesel it needs costly purification before being useful in most chemical applications.

Glycerol may be hydrotreated to form propane, which is useful as renewable LPG fuel, but the conversion required large amounts of hydrogen and the technical glycerol by-product from biodiesel production needs extensive purification before it can be hydroprocessed. LPG also has limited applications and there would thus be greater value if the glycerol could be converted to liquid transportation fuels such as gasoline, jet or diesel.

A need exists for a glycerol conversion process that can be used either to convert raw glycerol from soap or bio-diesel production into renewable transportation fuels, such as sustainable aviation fuels (SAF), or to renewable chemicals. The process herein enables the processing of raw low-cost glycerol with high impurities and water content without any significant pretreatment or water removal, while converting the glycerol into a product that can be processed directly in a hydrotreater without additional pre-treatment.

SUMMARY

In one aspect, there is provided a process for producing fuel-range organic compounds, the process comprising the steps of: (a) reacting a glycerol stream with a metal oxide catalyst at a temperature of from 300° C. to 700° C. and a pressure of from 100 kPa to 10 MPa to obtain a gaseous product mixture comprising one or more fuel-range organic oxygen-containing compounds, carbon dioxide, and one or more volatile organic compound by-products; and (b) separating the one or more fuel-range organic oxygen-containing compounds from the carbon dioxide and the one or more volatile organic compound by-products.

BRIEF DESCRIPTION OF THE DRAWINGS

FIG. 1 shows a boiling point distribution of fuel-range organic oxygen-containing compounds prepared according to Example 2.

DETAILED DESCRIPTION

Definitions

The term "renewable" refers to a natural resource that can be replenished within a 100-year time frame. The resource may be replenished naturally, or via agricultural techniques. Renewable resources include plants, animals, fish, bacteria, fungi, and forestry products. Fossil-based resources, such a crude oil (petroleum), natural gas, and coal, are not considered renewable resources. For clarity and for the purposes of the present disclosure, the terms "renewable", "bio-based", "non-petroleum", and "non-fossil-derived" may be used interchangeably.

The term "gasoline" can include hydrocarbons having a boiling point temperature in the range of about 25° C. to about 200° C. at atmospheric pressure.

As used herein the term "jet-range hydrocarbons", "jet-range paraffins", "jet-range fuels", or "jet fuels" can include hydrocarbons having a boiling point temperature in the range of about 150° C. to 300° C., preferably 200° C. to 300° C., at atmospheric pressure. Additionally, as used herein, the terms "jet-range hydrocarbons", "jet-range paraffins," "jet-range fuels", or "jet fuels" refer to a mixture of primarily C8 to C16 hydrocarbons with a maximum freezing point of about −40° C. or about −47° C.

The term "fuel-range" means hydrocarbons with a carbon number of from about C3 to about C18.

The term "ketone" refers to an organic compound with the structure RC(=O)R', where R and R' can be a variety of hydrocarbon substituents. The hydrocarbon substituent may be saturated or unsaturated, linear or branched linear, cyclic or acyclic, aromatic or non-aromatic. Ketones may also include molecules having two or more carbonyl moieties or other moieties containing oxygen, such a hydroxyl moiety. Also, included are hydrocarbon compounds with multiple ketone functions and with mixed ketone and monohydric functions (i.e., keto-monohydric aliphatic alcohol), with such keto-monohydric alcohols. The ketones most preferred are open chain ketones and other ketones having aliphatic groups wherein each aliphatic group is independently a linear or branched linear aliphatic group.

The term "volatile organic compound" ("VOC") is used to denote all organic materials which may be present in a gas phase at room temperature and atmospheric pressure such as hydrocarbons composed only of carbon and hydrogen, hydrocarbons containing nitrogen or oxygen, and the like.

The term "hydrodeoxygenation" refers to a catalytic process in which hydrogen is used to reduce the oxygen content of an oxygen-containing organic compound such as an ester, carboxylic acid, ketone, aldehyde, or alcohol. Complete hydrodeoxygenation of such compounds typically yields an alkane, in which the carbon atom(s) that previously was bonded to an oxygen atom becomes hydrogen-saturated (i.e., the carbon atom has become "hydrodeoxygenated").

The term "Cn hydrocarbons" or "Cn", is used herein having its well-known meaning, that is, wherein "n" is an integer value, and means hydrocarbons having that value of carbon atoms. The term "Cn+ hydrocarbons" or "Cn+" refers to hydrocarbons having that value or more carbon atoms. The term "Cn− hydrocarbons" or "Cn−" refers to hydrocarbons having that value or less carbon atoms.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

Glycerol Conversion

In the conversion step, glycerol is converted to one or more fuel-range organic oxygen-containing compounds by reacting a glycerol stream over a metal oxide catalyst under appropriate conditions.

The glycerol stream may be pure or impure. Crude glycerol is a natural by-product from the processing of fats and oils. For example, it is produced during transesterification of biodiesel production processes. Crude glycerol may contain impurities including water, inorganic salts such as chloride, sulfate, phosphate, acetate salts and others, organic compounds such as fatty acids, fatty esters, mono-glycerides, di-glycerides, phospholipids, protein residues, methanol, acids, bases, or combinations of any thereof. Impurities may account for from 10 wt. % to 50 wt. % of the crude glycerol. At least a portion of the impurities may be removed from the crude glycerol by a variety of treating methods, including neutralization, precipitation, filtration, evaporation, steam stripping, ion-exchange, adsorption, membrane separation, such as microfiltration, nanofiltration, osmosis and reverse osmosis, electro-deionization, and any combination. In some aspects, the glycerol stream is not subjected to any treating step prior to processing.

Fatty acid free glycerol is generally readily available in several grades: pharmaceutical (USP), food additive grade, and technical grade (industrial). The composition for USP glycerol on a dry basis must meet a 99.7% to 100% purity standard and any trace amounts of impurities must meet the USP specifications. Technical grade glycerol is typically purified (e.g., about 80% to about 97% pure) with most of its contaminants removed (e.g., methanol, soaps, salts, etc.).

The glycerol stream may comprise at least 10 wt. % (e.g., at least 20 wt. %, or at least 30 wt. %, or at least 40 wt. %, or at least 50 wt. %, or at least 60 wt. %, or at least 70 wt. %, or at least 80 wt. %, or at least 90 wt. %, or at least 95 wt. %, or at least 99 wt. %) glycerol.

The glycerol stream may be contacted with liquid or vaporous water (i.e., steam) so that the resulting feed stream comprises up to 30 wt. % (e.g., 0.1 wt. to 30 wt. %, or 0.5 to 20 wt. %) water, based on a total weight of the feed stream. If the glycerol stream is fed in liquid form to the reactor, water is preferably fed in the form of steam, whereby the steam is sprayed into the glycerol stream or the glycerol stream is sprayed into the steam.

Any suitable catalyst for converting glycerol may be used. For example, the catalyst can be a metal oxide catalyst. Representative metal oxides include alumina, silica-alumina, niobium oxide, titania, and zirconia. The metal oxide catalyst can also include a modifier to enhance selectivity and/or activity. Suitable modifiers include La, Y, Sc, Li, Na, K, Rb, Cs, Mg, Ca, Sr, Ba, and any combination thereof. The amount of modifier may be in a range of from 0.1 wt. % to 20 wt. % (e.g., 0.25 wt. % to 10 wt. %, or 0.5 wt. % to 5 wt. %), based on the total weight of the catalyst composition.

The metal oxide catalyst can have a surface area in a range of from 10 m$^2$/g to 400 m$^2$/g (e.g., 20 m$^2$/g to 200 m$^2$/g, or 50 m$^2$/g to 200 m$^2$/g).

The catalyst may be in any of the commonly used catalyst shapes such as, for example, spheres, granules, pellets, chips, rings, extrudates, or powders that are well-known in the art.

The catalyst may be regenerated by heating in the presence of an oxygen-containing gas at a temperature of from 375° C. to 550° C. Steam may be concurrently introduced during regeneration.

The reactor can be any reactor format known in the art to be suitable for gas-phase endothermic reactions. For example, the reactor may be conducted using a fixed, fluidized, or moving bed reactor. In some aspects, glycerol conversion can be carried out in a single-stage adiabatic fixed-bed reactor, a multiple-stage adiabatic reactor, or a tubular fixed bed reactor. Because the glycerol conversion is endothermic, the reactor can be operated in an adiabatic mode.

The reactor may be operated at a temperature of from 300° C. to 700° C. (e.g., 350° C. to 600° C.)

The pressure may be in a range of from 100 kPa to 10 MPa (e.g., 100 kPa to 5 MPa).

In the reactor, glycerol is converted to into a gaseous product mixture comprising fuel-range organic oxygen-containing compounds, carbon dioxide, and one or more volatile organic compounds. The fuel-range organic oxygen-containing compounds can be separated from the carbon dioxide and the VOCs by conventional methods known in the art. For example, the gaseous product mixture from the reactor can be separated by direct condensation to produce a liquid stream comprising crude fuel-range organic oxygen-containing compounds and a gaseous by-product stream carbon comprising carbon dioxide and the volatile organic compounds. In one aspect, the separation step comprises cooling the gaseous product mixture by contact with a heat exchanger or a solvent. For example, fuel-range organic oxygen-containing compounds may be condensed by indirect cooling in a heat exchanger against water, chilled brine, chilled glycol, or the like, or via direct contact cooling with an injected solvent such as water. After cooling, phase separation produces a by-product carbon dioxide stream comprising predominantly non-condensable components (carbon dioxide and volatile organic compounds) and a liquid stream comprising crude fuel-range organic oxygen-containing compounds.

According to the present process, much of the oxygen from the glycerol is ejected in form of $CO_2$ and the residual oxygen found in the product is primarily in form of C3-C12 ketones with a minor amount of C6-12 phenol derivatives. In some aspects, the fuel-range organic oxygen-containing compounds comprises at least at least 50 wt. % (e.g., at least 60 wt. %, or at least 70 wt. %, or at least 80 wt. %, or at least 90 wt. %, or at least 95 wt. %) C3-12 ketones. In some aspects, the fuel-range organic oxygen-containing compounds comprises less than 40 wt. % (e.g., less than 30 wt. %, less than 20 wt. %, or less than 10 wt. %, or less than 5 wt. %) C6-C12 phenols.

After condensation and separation of the carbon dioxide by-product, the liquid stream comprising crude fuel-range organic oxygen-containing compounds can be distilled to produce one or more fractions boiling in the gasoline or jet range.

After condensation and separation of the carbon dioxide by-product, the liquid stream comprising crude fuel-range organic oxygen-containing compounds may be fractionated (e.g., by distillation) into different fractions, each of which is known to be within a certain boiling point range. For example, fractionation may be conducted at a determined fractionation temperature or boiling point cut-off to separate out various boiling point fractions appropriate to a desired fuel product and to collect light products for further processing. Distillate fractions can be in any or all of the naphtha, jet, diesel, or other fuel ranges. These fractions can be hydroprocessed to provide paraffin and isoparaffin fuels or fuel blend stocks.

In some aspects, fractionation may be conducted upon completion of all other post-processing (e.g., hydroprocessing) in order to more accurately control the composition of the collected fractions. Such control might be desirable, for example, if a specific boiling point range were desired to meet the specifications of a desired fuel type.

Hydroprocessing

Fuel-range organic oxygen-containing compounds obtained from the glycerol conversion step may be subjected to a catalytic hydroprocessing step to provide hydrocarbons, suitable as renewable fuels or fuel components, useful as transportation fuels, fuel components and other chemicals.

The catalytic hydroprocessing comprises at least a hydrodeoxygenation (HDO) step.

The hydrodeoxygenation reaction may be carried out in the presence of hydrogen gas and a hydrodeoxygenation catalyst, such as CoMo, NiMo, NiW, CoNiMo on a support (e.g., alumina, silica, alumina-silica, zirconia). The hydrodeoxygenation step may be conducted at a temperature of from 100° C. to 500° C. (e.g., 250° C. to 400° C.), and at a pressure of from 2 MPa to 15 MPa (e.g., 4 MPa to 10 MPa), a weight hourly space velocity (WHSV) of from 0.1 $h^{-1}$ to 10 $h^{-1}$ (e.g., 0.2 $h^{-1}$ to 5 $h^{-1}$), and a hydrogen flow of from 350 to 900 NL $H_2$/L feed, using a catalyst, such as NiMo, optionally on a alumina support.

Water and light gases may be separated from the HDO product with any conventional means such as distillation. After the removal of water and light gases, the HDO product may be fractionated to one or more fractions suitable for use as gasoline, aviation fuel, diesel or heavy oil components. The fractionation may be conducted by any suitable means, such as distillation. Optionally, part of the product of the HDO step may be recycled and combined to the feed of the HDO reactor.

Catalytic hydroprocessing may also comprise an isomerization step in the presence of hydrogen and an isomerization catalyst. Both the HDO step and isomerization step may be conducted in the same reactor. In some aspects, the isomerization catalyst is a noble metal bifunctional catalyst (e.g., Pt-SAPO-11, Pt-ZSM-48). The isomerization step may be conducted at a temperature of from 200° C. to 400° C. and at a pressure of 2 MPa to 15 MPa. Fractionation may be carried out before or after isomerization but is preferably carried out after isomerization. Preferably, no isomerization step is carried out.

EXAMPLES

The following illustrative examples are intended to be non-limiting.

Example 1

Catalyst Preparation

Alumina was wetted to incipient wetness with a calcium acetate solution containing 10 g $(CH_3CO_2)_2Ca$ dissolved in 50 mL water, dried in air at 120° C.-150° C., and calcined at 900° F. to give a calcium-promoted alumina catalyst.

Example 2

A fixed bed reactor was charged with 50 $cm^3$ of the calcium-promoted alumina catalyst of Example 1. Glycerol and steam were each fed to the reactor at a rate of 1 g/minute. The reactor was operated at 900° F. and atmospheric pressure. The reactor effluent was cooled to ambient temperature producing an oil, an aqueous phase and a gas stream.

Effluent was analyzed by Gas Chromatography-Mass Spectrometry (GC-MS).

The oil yield was 15-25 wt. % relative to glycerol converted. FIG. 1 shows a GC-boiling curve of the recovered oil product. The oil contained about 50% ketones and aldehydes, about 30% phenol derivatives (e.g., alkylphenols, polyalkylphenols, phenolic ethers), and about 20% hydrocarbons.

An additional 10-15 wt. % relative to the oil phase of mostly light carbonyls (e.g., acetaldehyde, acetone, methyl ethyl ketone, diethyl ketone, methyl propyl ketone, methyl isopropyl ketone) were extracted from the aqueous phase (<5 wt. % relative to glycerol converted). When combining extractable organics from the water phase with the oil phase content, light C3-O5 ketones (e.g., acetone, methyl ethyl ketone, pentanones) constituted about a quarter of the total recovered liquid product by weight.

The gas stream contained light hydrocarbons (C1-C4) in an amount corresponding to a yield of about 5-10 wt. %, relative to glycerol converted, and $CO_2$ in an amount corresponding to about 30-35 wt. % yield, relative to glycerol converted.

The product mixture is surprisingly rich in compounds boiling in the naphtha and jet boiling range and with substantially lower oxygen content than the glycerol feedstock. Surprisingly, much of the oxygen from the glycerol is ejected in form of $CO_2$ and the residual oxygen found in the product is mostly in form of ketones (cyclic and acyclic, saturated and unsaturated, 3 to 12 carbons per molecule), and to a lesser extend as phenol derivatives (6-12 carbons per molecule).

The high $CO_2$ make is both unexpected and valuable. It has the advantage that the organic products produced have a higher hydrogen/carbon ratio than could have been achieved through simple dehydration of the glycerol. The ability for the process to eject the oxygen from the glycerol largely as $CO_2$ as opposed to as water is responsible for the ability to produce a product rich in high value components such as the C3-C5 ketones. In addition, if the glycerol conversion is intended to make fuel products, the ejection of oxygen as $CO_2$ significantly diminishes the hydrogen requirements and reaction exotherm in subsequent hydroprocessing.

The invention claimed is:

1. A process for producing distillate-range organic compounds, the process comprising the steps of:
   (a) reacting a glycerol stream with a metal oxide catalyst at a temperature of from 300° C. to 700° C. and a pressure of from 100 kPa to 10 MPa to obtain a gaseous product mixture comprising one or more fuel-range organic oxygen-containing compounds, carbon dioxide, and one or more volatile organic compound by-products; and
   (b) separating the one or more fuel-range organic oxygen-containing compounds from the carbon dioxide and the one or more volatile organic compound by-products;

the metal oxide catalyst consisting of (i) a metal oxide selected from the group consisting of alumina, silica-alumina, niobium oxide, titania, zirconia, and any combination thereof; and (ii) 0.1 wt. % to 20 wt. % of a modifier selected from the group consisting of La, Y, Sc, Li, Na, K, Rb, Cs, Mg, Ca, Sr, Ba, and any combination thereof, based a total weight of the catalyst; wherein the glycerol stream comprises at least 70 wt. % glycerol; and wherein the one or more fuel-range organic oxygen-containing compounds comprise at least 50 wt. % C3-C12 ketones.

2. The process of claim 1, wherein the glycerol stream is not subjected to a treating step.

3. The process of claim 2, wherein the treating step is selected from neutralization, precipitation, filtration, evaporation, steam stripping, ion-exchange, adsorption, membrane separation, and any combination thereof.

4. The process of claim 1, wherein step (a) is conducted in the presence of water and/or steam.

5. The process of claim 1, wherein step (a) is conducted in a fixed-bed reactor.

6. The process of claim 1, wherein step (b) comprises cooling the gaseous product mixture by contact with a heat exchanger or a solvent.

7. The process of claim 1, further comprising hydrodeoxygenating the one or more fuel-range organic oxygen-containing compounds to form a deoxygenated product comprising hydrocarbons.

8. The process of claim 7, wherein the hydrodeoxygenating is performed at a temperature of from 100° C. to 500° C.; a pressure of from 2 MPa to 15 MPa; a WHSV of from $0.1\ h^{-1}$ to $10\ h^{-1}$; and a hydrogen flow of from 350 to 900 NL $H_2$/L feed, in a presence of a hydrodeoxygenation catalyst.

9. The process of claim 7, further comprising distilling the deoxygenated product stream to obtain one or more of gasoline and jet fuel.

10. The process of claim 1, wherein the glycerol stream comprises at least 95 wt. % glycerol.

11. The process of claim 1, wherein the one or more fuel-range organic oxygen-containing compounds comprise at least 95 wt. % C3-C12 ketones.

\* \* \* \* \*